(12) United States Patent
Mok et al.

(10) Patent No.: US 11,085,068 B2
(45) Date of Patent: Aug. 10, 2021

(54) METHOD FOR GENERATING SINGLE-STRANDED CIRCULAR DNA LIBRARIES FOR SINGLE MOLECULE SEQUENCING

(71) Applicant: Roche Sequencing Solutions, Inc., Pleasanton, CA (US)

(72) Inventors: Janine Mok, Palo Alto, CA (US); Ulrich Schlecht, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 94 days.

(21) Appl. No.: 16/252,258

(22) Filed: Jan. 18, 2019

(65) Prior Publication Data
US 2019/0153514 A1    May 23, 2019

Related U.S. Application Data

(63) Continuation of application No. PCT/EP2017/067940, filed on Jul. 14, 2017.

(60) Provisional application No. 62/363,645, filed on Jul. 18, 2016.

(51) Int. Cl.
*C12Q 1/6806* (2018.01)
*C12Q 1/6869* (2018.01)
*C12N 15/10* (2006.01)

(52) U.S. Cl.
CPC ....... *C12Q 1/6806* (2013.01); *C12N 15/1093* (2013.01); *C12Q 1/6869* (2013.01); *C12N 2310/532* (2013.01)

(58) Field of Classification Search
None
See application file for complete search history.

(56) References Cited

U.S. PATENT DOCUMENTS

| 7,302,146 B2 | 11/2007 | Turner et al. |
| 8,153,375 B2 | 4/2012 | Travers et al. |
| 2010/0069263 A1 | 3/2010 | Shendure et al. |

FOREIGN PATENT DOCUMENTS

| WO | 2008/096146 A1 | 8/2008 | |
| WO | 2009/120372 A2 | 10/2009 | |
| WO | WO-2009120372 A2 * | 10/2009 | ............. C12Q 1/689 |
| WO | 2009/133466 A2 | 11/2009 | |
| WO | WO-2009133466 A2 * | 11/2009 | ........... C12Q 1/6855 |
| WO | 2012/012037 A1 | 1/2012 | |
| WO | 2015/089333 A1 | 6/2015 | |
| WO | WO-2015089333 A1 * | 6/2015 | ........... C12Q 1/6869 |
| WO | 2017100441 A1 | 6/2017 | |

OTHER PUBLICATIONS

International Search Report and Written Opinion dated Oct. 4, 2017 in PCT/EP2017/067940 filed Jul. 14, 2017, pp. 1-13.

* cited by examiner

*Primary Examiner* — Kaijiang Zhang
(74) *Attorney, Agent, or Firm* — Eric Grant Lee; Olga Kay

(57) ABSTRACT

The invention comprises circular single-stranded templates for nucleic acid sequencing, methods of making and using the same.

10 Claims, 5 Drawing Sheets

METHOD FOR GENERATING SINGLE-STRANDED CIRCULAR DNA LIBRARIES FOR SINGLE MOLECULE SEQUENCING

CROSS-REFERENCE TO RELATED APPLICATIONS

This application is a continuation of International Patent Application No. PCT/EP2017/067940 filed Jul. 14, 2017, which is based on and claims the benefit of U.S. Provisional Application No. 62/363,645, filed on Jul. 18, 2016, the contents of which are hereby incorporated by reference in their entirety.

FIELD OF THE INVENTION

The invention relates to the field of nucleic acid sequencing and more specifically, to preparing circular templates for nucleic acid sequencing.

BACKGROUND OF THE INVENTION

The use of circular templates for sequencing is known in the art. For example, PACIFIC BIOSCIENCES uses a SMRTBELL adaptor to produce such templates. See U.S. Pat. Nos. 7,302,146 and 8,153,375. Circular single-stranded templates have several advantages in sequencing by synthesis: if a sequencing polymerase can perform rolling circle replication, the template will be read multiple times and both Watson and Crick strands will be read. The multiple reads of paired strands promise more accurate consensus sequence output. However, the existing circular templates are designed such that two sequencing polymerases can bind to each template. The two polymerases have the potential to interfere with each other and cause stalling or termination of synthesis generating suboptimal sequencing data. The present invention improves upon the existing technology to enable more accurate sequencing reads.

SUMMARY OF THE INVENTION

In one embodiment, the invention is a method of preparing a target nucleic acid for sequencing comprising providing a sample comprising the target nucleic acid; contacting the sample with an adaptor molecule comprising two strands, forming at least one duplex region and at least one non-duplex region, the non-duplex region comprising at least one universal primer binding site; and ligating the adaptor molecule to the target nucleic acid to form a double-stranded circular joint molecule comprising the non-duplex region with the at least one universal primer binding site. The method may further comprise contacting the joint molecule with a DNA polymerase and a universal primer complementary to the primer binding site; and extending the universal primer thereby determining the sequence of the target nucleic acid via sequencing by synthesis. The adaptor may comprise two duplex regions flanking a single non-duplex region having two unhybridized strands. The adaptor alternatively, may comprise two duplex regions flanking at least one stem-loop structure, each structure comprising a duplex stem region and a non-duplex loop region. Each strand of the adaptor may comprise one primer binding site. The two strands have the same primer binding site or have different primer binding sites. The ligation can be a blunt-end ligation or a cohesive-end ligation. In some embodiments, the method comprises a preliminary step of adding in a template-independent manner, a nucleotide to the 3'-termini of the target nucleic acid and a complementary nucleotide to the 3'-termini of the adaptor molecule thereby creating cohesive ends. In other embodiments, the method comprises a preliminary step of digesting the target nucleic acid and the adaptor molecule with a restriction endonuclease to generate compatible cohesive ends. In other embodiments, the method comprises a preliminary step of digesting the 3'-termini of the target nucleic acid and the adaptor molecule with an exonuclease. In some embodiments, the target nucleic acid comprises at least one phosphorothioate nucleotide near the 3'-end. In some embodiments, the target nucleic acid and the adaptor molecule contain uracil bases and the method comprises prior to step b), a step of contacting the target nucleic acid and the adaptor molecule with an N-glycosylase and an AP-lyase. For example, the target nucleic acid and the adaptor molecule are contacted with Uracil-DNA-glycosylase and Endonuclease VIII or Uracil-DNA-glycosylase and a polyamine and exposed to heat. In some embodiments, the polymerase is a strand-displacing polymerase. In some embodiments, the sample comprises a plurality of target nucleic acids. In some embodiments the target nucleic acid is fragmented prior to commencing the steps of the method.

In some embodiments, the target nucleic acid is subjected to end repair by a DNA polymerase prior to commencing the steps of the method. The adaptor may comprise one or more barcodes, Unique Identifier (UID), Multiplex Identifier (MID), or a combination thereof.

In some embodiments, the invention is a method of preparing a target nucleic acid for sequencing comprising providing a sample comprising the target nucleic acid; contacting the sample with an adaptor molecule comprising two strands forming a duplex wherein each strand comprises a universal primer binding site; ligating the adaptor molecule to the target nucleic acid to form a double-stranded circular joint molecule comprising two universal primer binding sites. In some embodiments, the method further comprises contacting the joint molecule with a DNA polymerase and universal primers complementary to the primer binding sites; extending the universal primers thereby determining the sequence of the target nucleic acid via sequencing by synthesis. In some embodiments, each strand has the same primer binding site. In other embodiments, the two strands have different primer binding sites.

In some embodiments, the invention is a composition for sequencing a target nucleic acid comprising a double-stranded circular molecule consisting of the target nucleic acid ligated to an adaptor comprising two strands, wherein the strands form at least one duplex region and at least one non-duplex region, each strand in the non-duplex region containing a universal primer binding sites. The composition may also comprise one or more of a universal primer and a nucleic acid polymerase with strand-displacement activity.

DETAILED DESCRIPTION OF THE INVENTION

Definitions

Figure 1:
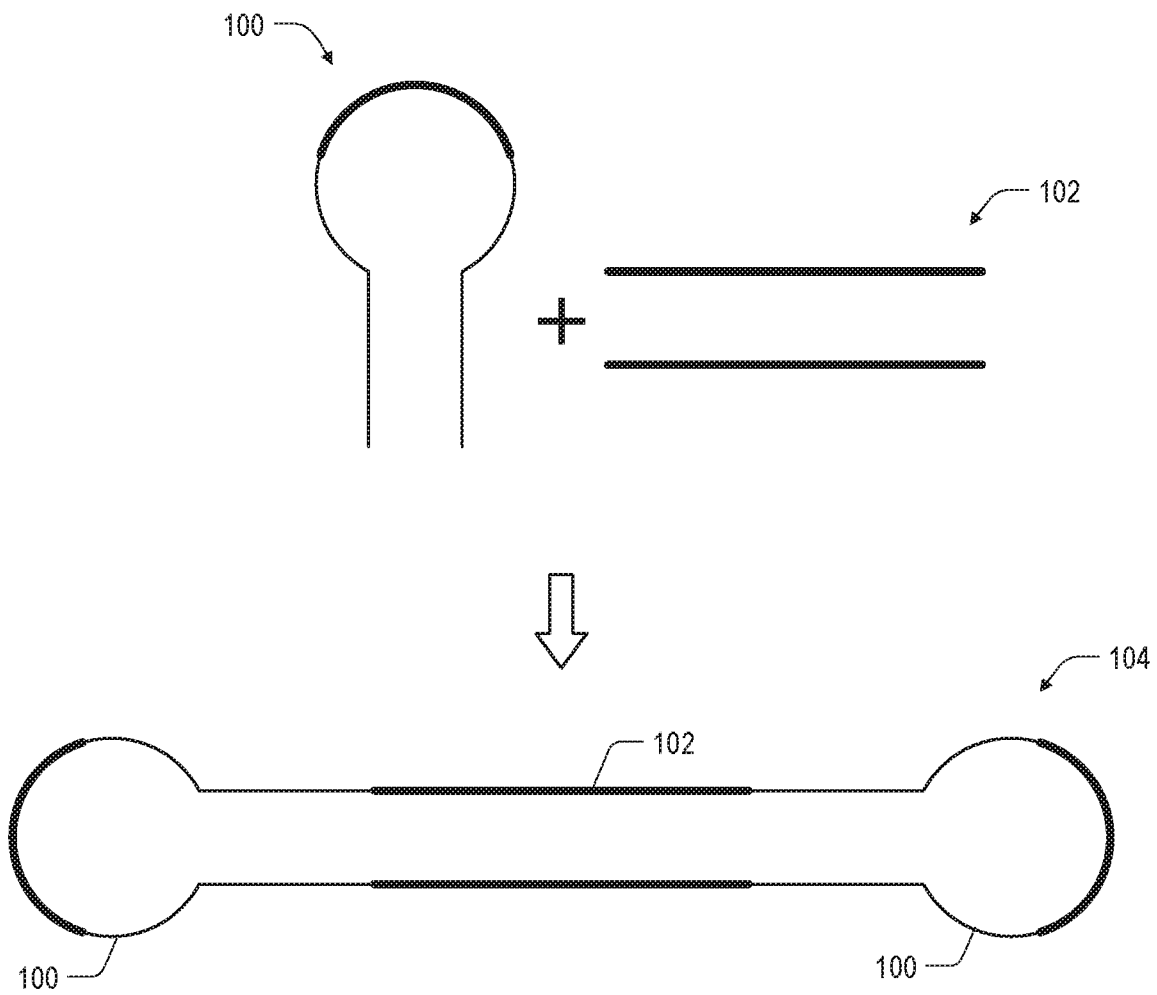
FIG. 1 is a diagram of a prior art method of assembling a circular molecule using two stem-loop adaptors.

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

A term "nucleic acid" refers to polymers of nucleotides (e.g., ribonucleotides and deoxyribonucleotides, both natural and non-natural) such polymers being DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil, and thymidine) as well as non-natural bases. Some examples of non-natural bases include those described in, e.g., Seela et al., (1999) *Helv. Chim. Acta* 82:1640. The non-natural bases may have a particular function, e.g., increasing the stability of the duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. An oligonucleotide may be comprised of at least 6 nucleotides, for example at least about 10-12 nucleotides, or at least about 15-30 nucleotides. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191.

The terms "duplex" and "double-stranded region" are used interchangeably to refer to a region where two nucleic acid strands are hybridized. The strands need not be perfectly complementary to maintain the duplex. Depending on the sequence, two nucleic acid strands can form a structure containing duplex regions and non-duplex regions.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes are typically incorporated into other nucleic acids. Barcodes are sufficiently long e.g., 2, 5, 10 nucleotides, so that the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" refer to a primer and primer binding site present in (typically, through being artificially added to) different target nucleic acids. The universal priming site is added to the target nucleic acid using adaptors or target-specific (non-universal) primers having a 5'-flap region. The universal primer can bind to and direct primer extension from the universal priming site.

The term "cohesive ends" refers to single-strand overhangs on the ends of a first double-stranded nucleic acid capable of forming a duplex with single-strand overhangs on the ends of a second double-stranded nucleic acid such that the two nucleic acids can be joined, e.g., by ligation, optionally with polymerase extension of the ends. Cohesive ends of the two molecules need not be perfectly complementary for the two molecules to be joined.

The terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "sequencing" refers to any method of determining the sequence of nucleotides in the target nucleic acid.

The present invention provides a method of preparing a target nucleic acid for sequencing comprising
  (a) providing a sample comprising the target nucleic acid;
  (b) contacting the sample with an adaptor molecule comprising two strands, forming at least one duplex region and at least one non-duplex region, the non-duplex region comprising at least one universal primer binding site; and (c) ligating the adaptor molecule to the target nucleic acid to form a double-stranded circular joint molecule comprising the non-duplex region with the at least one universal primer binding site.

The method may further comprise the steps of (d) contacting the joint molecule with a DNA polymerase which may be a strand-displacing polymerase, and a universal primer complementary to the primer binding site; and (e) extending the universal primer thereby determining the sequence of the target nucleic acid via sequencing by synthesis.

The adaptor may comprise two duplex regions flanking a single non-duplex region having two unhybridized strands. The adaptor may also comprise two duplex regions flanking at least one stem-loop structure, each structure comprising a duplex stem region and a non-duplex loop region. Each strand of the adaptor ma comprises one primer binding site.

The ligation may be a blunt-end ligation or preferably a cohesive-end ligation. In this case, the inventive method may comprise prior to step b), a step of adding in a template-independent manner, a nucleotide to the 3'-termini of the target nucleic acid and a complementary nucleotide to the 3'-termini of the adaptor molecule thereby creating cohesive ends. The inventive method may also comprise prior to step b) a step of digesting the target nucleic acid and the adaptor molecule with a restriction endonuclease to generate compatible cohesive ends. The inventive method may also comprise prior to step b) a step digesting the 3'-termini of the target nucleic acid and the adaptor molecule with an exonuclease. Then, the target nucleic acid may comprise at least one phosphorothioate nucleotide. The target nucleic acid and the adaptor molecule may contain uracil bases and the method may comprise prior to step b), a step of contacting the target nucleic acid and the adaptor molecule with an N-glycosylase and an AP-lyase. Which may be Uracil-DNA-glycosylase and Endonuclease VIII. The target nucleic acid and the adaptor molecule may be contacted with Uracil-DNA-glycosylase and a polyamine compound at elevated temperature.

The sample may comprises a plurality of target nucleic acids. The target nucleic acid is fragmented prior to step b) and may be subjected to end repair by a DNA polymerase prior to step b). The adaptor may comprise one or more barcodes which may include one or more of a Unique Identifier (UID), Multiplex Identifier (MID) or a combination thereof.

The present invention also provides a method of preparing a target nucleic acid for sequencing comprising (a) providing a sample comprising the target nucleic acid;

(b) contacting the sample with an adaptor molecule comprising two strands forming a duplex wherein each strand comprises a universal primer binding site; and (c) ligating the adaptor molecule to the target nucleic acid to form a double-stranded circular joint molecule comprising two universal primer binding sites.

The method may further comprise the steps of (d) contacting the joint molecule with a DNA polymerase and universal primers complementary to the primer binding sites; and (e) extending the universal primers thereby determining the sequence of the target nucleic acid via sequencing by synthesis.

Each strand may have the same or a different primer binding site.

The present invention further provides a composition for sequencing a target nucleic acid comprising a double-stranded circular molecule consisting of the target nucleic acid ligated to an adaptor comprising two strands, wherein the strands form at least one duplex region and at least one non-duplex region, each strand in the non-duplex region containing a universal primer binding sites. The composition may further comprise a universal primer, or a nucleic acid polymerase with strand-displacement activity or both.

In some embodiments, the present invention is a method converting a double-stranded target nucleic acid into a circular locked strand template useful in sequencing. The use of circular templates is known in the art and has several advantages in sequencing by synthesis applications. See U.S. Pat. Nos. 7,302,146 and 8,153,375. If a strand displacing polymerase is used, it will engage in rolling circle replication, i.e., continuously displace the nascent strand, and perform multiple rounds of copying the circular template. The ability to sequence (read through) the target multiple times and compare both Watson and Crick strands of a nucleic acid linked into the circular structure allows to generate error-free or low-error consensus sequences.

However, with reference to FIG. 1, the existing circular templates are designed to have an adaptor 100 ligated to both ends of the target nucleic acid 102 so that the resulting circular molecule 104 contains two adaptor sequences 100. (FIG. 1). Each adaptor has a binding site for the sequencing primer allowing the binding of two primers and two DNA polymerases to each circular template. Once the sequencing reaction has started, the two polymerases have the potential to interfere with each other and cause stalling or termination of synthesis, decreasing read-length and the yield of sequencing data. This is especially problematic with shorter templates where two polymerases land in relative proximity to each other.

One way of assembling circular molecules for sequencing has been converting each of the two strands of the double-stranded target nucleic acid into a separate circular molecule having a single adaptor sequence. See US20120003675 and U.S. Pat. No. 7,883,849. This approach requires complementarity between the arms of the adaptor and the target nucleic acid so that the single strand could be linked into a circle. This approach is not practical for creating a library of a plurality of nucleic acids of unknown sequence.

Figure 3:
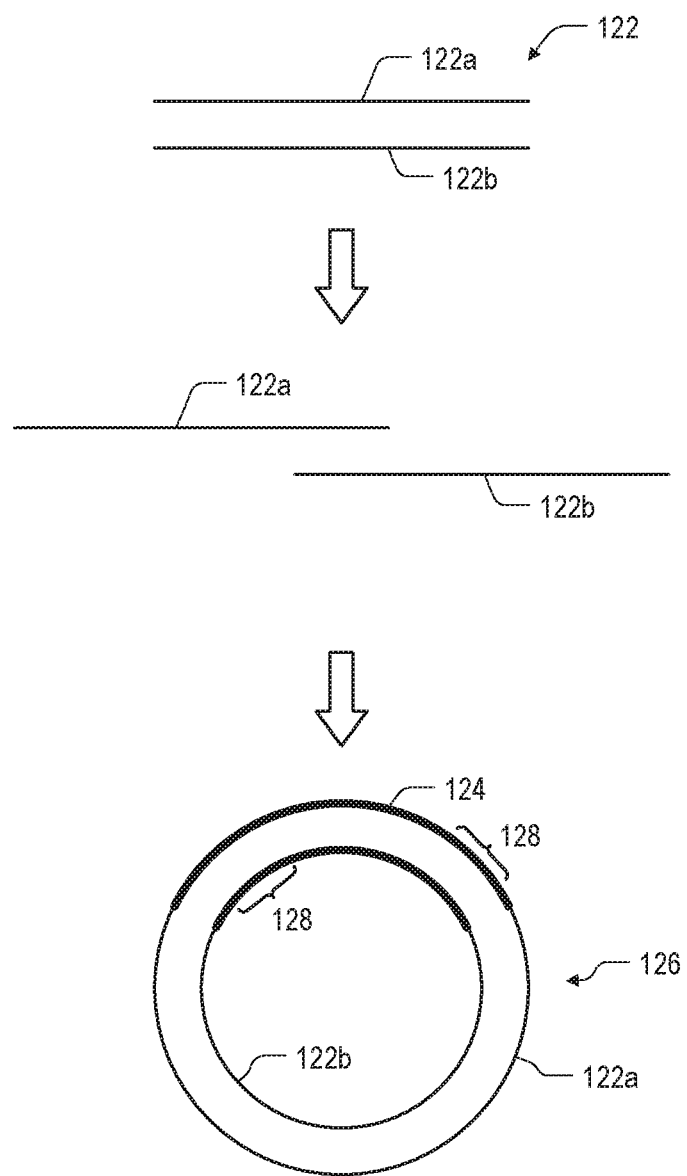
FIG. 3 is a diagram of the novel method of assembling a circular molecule using a single double-stranded adaptor.
Figure 4:
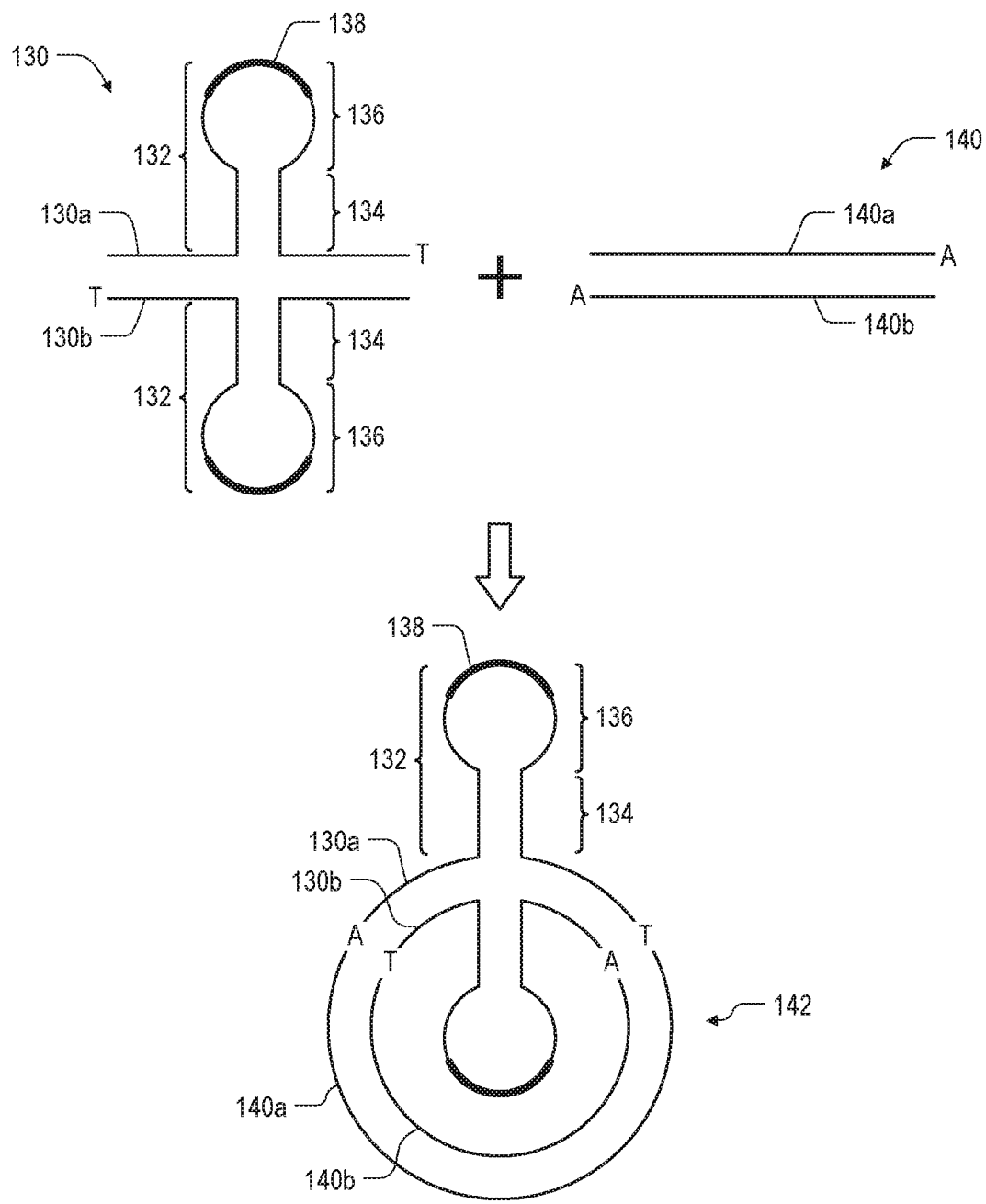
FIG. 4 is a diagram of the novel method of assembling a circular molecule using a single adaptor having two double-stranded regions and two stem-loop regions.
Figure 5:
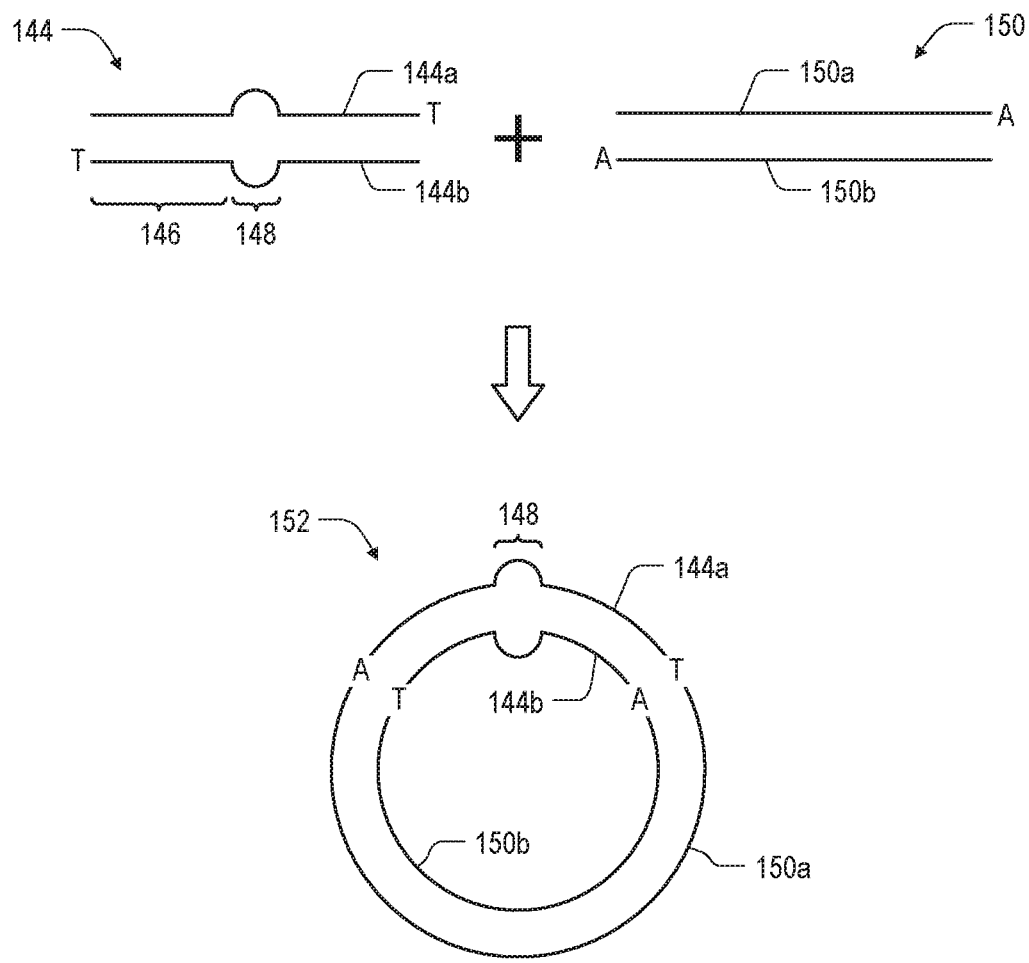
FIG. 5 is a diagram of the novel method of assembling a circular molecule using a single adaptor having two double-stranded regions flanking a single-stranded region.

The present invention is a novel method that allows the formation of a library of circular molecules which regardless of sequence comprise a single primer binding site for the sequencing polymerase. (FIGS. 3, 4 and 5). The present invention is a novel method that may increase sequencing quality, read-length, and efficiency. In the embodiments of the invention, each double-stranded target nucleic acid is conjugated to a single adaptor. The resulting circular double-stranded molecule comprises two strands, each having a single primer binding site where sequencing is to be initiated.

The present invention comprises modifying and sequencing a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples), The sample may comprise whole blood or blood fractions where tumor cells may be present. In some embodiments, the sample, especially a liquid sample may comprise cell-free material such as cell-free DNA or RNA including cell-free tumor DNA or cell-free tumor RNA. In some embodiments, the sample is a cell-free sample, e.g., cell-free blood fraction where cell-free tumor DNA or cell-free tumor RNA is present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus, or a mycoplasma.

The target nucleic acid is isolated, i.e., separated from other tissue and cellular components to enable enzymatic reactions described herein to occur. The isolation may be performed by any suitable method known in the art.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism or a mutation, including a single nucleotide polymorphism or variant (SNP of SNV), or a genetic rearrangement resulting in a gene fusion. In some embodiments, the target nucleic acid comprises a biomarker, i.e., a gene or gene variant associated with a disease or condition. In other embodiments, the target nucleic acid is characteristic of a particular organism and aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype.

In one embodiment of the invention, a double-stranded target nucleic acid is converted into the template configuration of the invention. In other embodiments, the target nucleic acid occurs in nature in a single-stranded form (e.g., RNA, including mRNA, microRNA, viral RNA; or single-stranded viral DNA). The single-stranded target nucleic acid is converted into double-stranded form prior to the commencement of the other steps of the method described herein. Longer target nucleic acids may be fragmented although in some applications longer target nucleic acids may be desired to achieve a longer read. In some embodiments, the target nucleic acid is naturally fragmented, e.g., circulating cell-free DNA (cfDNA) or chemically degraded nucleic acid such as the one found in chemically preserved samples (formalin-fixed paraffin embedded tissues, FFPET).

In the embodiments of the present invention, the adaptor molecule is ligated to a molecule of the target nucleic acid. Both ends of the target nucleic acid are ligated to the ends of a single adaptor thereby forming a joint molecule. The composition of the reaction mixture is such that the kinetics of the ligation reaction favor ligating one target nucleic acid to a single adaptor. The single adaptor ligation is favored over self-circularization and ligation to two adaptors. In some embodiments, the concentration of the target nucleic acid in the sample is estimated or quantified and a suitable molar amount of the adaptor is added. In some embodiments, the target to adaptor ratio is 1/20, 1/200 or 1/400. One of skill in the art will understand that a cohesive end ligation is more efficient and will require a smaller concentration of the adaptor compared to the blunt end ligation.

In some embodiments, the adaptor and the target nucleic acid or only the adaptor are pre-treated to allow the formation of the joint molecule but prevent self-ligation including adaptor dimerization and self-circularization of the target nucleic acid. In some embodiments, the adaptor is modified with a 3'-phosphate group to prevent dimerization. In other embodiments, the target nucleic acid is treated with alkaline phosphatase to remove the 5'-phosphate group and prevent self-circularization.

In some embodiments, the ligation occurs in two steps: the first step is ligation of the adaptor and the second step is self-circularization of the ligated joint molecule. In some embodiments, the unligated adaptors are separated from the joint molecules after the first step. In some embodiments, the separation is by chromatography or electrophoresis. In some embodiments the unligated target nucleic acids or unligated adaptors are removed after the final ligation step, e.g., by exonuclease digestion. In some embodiments, the self-circularized target nucleic acid is not removed as it contains no primer binding sites and will not interfere with the subsequent steps of the method.

The ligation can be a blunt-end ligation or a more efficient cohesive-end ligation. The target nucleic acid or the adaptors may be rendered blunt-ended by strand-filling, i.e., extending the 3'-terminus by a DNA polymerase to eliminate any 5'-overhangs.

In some embodiments, the ends of the adaptors and the target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends by digestion with restriction endonucleases. The latter option is more advantageous for known target sequences that are known to contain the restriction enzyme recognition site. In some embodiments, the target nucleic acid may be contacted with an exonuclease under the conditions favorable for removal of one or more nucleotides from one end of one or both strands of the target nucleic acid thus creating cohesive ends. In some embodiments, the exonuclease digestion of the ends of the target nucleic acid may be controlled, e.g., by controlling the time of digestion or through incorporation of exonuclease resistant nucleotides. In some embodiments, the target nucleic acid is copied or amplified using a primer containing one or more exonuclease-resistant phosphorothioate nucleotides. In one embodiment, the cohesive ends are created in the target nucleic acid by a combination of a glycosylase and an AP lyase. In that embodiment, the target nucleic acid contains a nucleotide suitable for base excision by the glycosylase (e.g., a deoxyuridine base suitable for excision by Uracil-N-DNA glycosylase). In some embodiments, the base excision reaction is followed by thermal or enzymatic breakage of the phosphodiester backbone at the abasic site. In some embodiments the sample is contacted with Endonuclease VIII under the conditions favoring endonucleolytic cleavage of the abasic site. In other embodiments, the DNA with the abasic site is subjected to thermal degradation. In some embodiments, non-enzymatic enhancers of thermal degradation of abasic DNA such as polyamine compounds can be added, see U.S. Pat. No. 8,669,061.

In each of the above embodiments, the adaptor molecule may acquire the desired ends (blunt, single-base extension, or multi-base overhang) through design and in vitro synthesis of the adaptor oligonucleotides further described below.

In some embodiments, other enzymatic steps may be required to accomplish the ligation. In some embodiments, a polynucleotide kinase may be necessary to add 5'-phosphates to one or both of the target nucleic acid molecules and adaptor molecules.

The present invention comprises the use of adaptor molecules to be ligated to one or both ends of the target nucleic acid. In some embodiments, the adaptor comprises two complementary strands forming a double-stranded structure. For example, with reference to FIG. 3, a double-stranded DNA fragment 122 having a plus strand 122a and a minus strand 122b can be optionally denatured to provide two single-stranded molecules (i.e., the plus strand 122a and the minus strand 122b). Thereafter, the double-stranded DNA fragment 122 (or each of the plus strand 122a and the minus strand 122b) can be combined with an adaptor 124 (e.g., via ligation) to provide the double-stranded circular molecule 126. In one aspect, each strand of the adaptor 124 can include a single primer binding site 128 where sequencing is to be initiated.

Turning to FIG. 4, in some embodiments, an adaptor 130 has a cross-like structure including a first strand 130a and a second strand 130b. Each of the strands 130a and 130b can adopt a stem-loop secondary structure 132 comprising at least one double-stranded region 134 and at least one single-stranded region 136. The double-stranded region 134 comprises a region of at least partial self-complementarity ensuring the stability of the secondary structure under reaction conditions employed herein. In another aspect, the ends of the strands 130a and 130b can be at least partially complimentary to each other in order to provide the cross-like structure shown in FIG. 4. In yet another aspect, each strand of the adaptor 130 can include a single primer binding site 138 where sequencing is to be initiated. In one example, the primer binding site 138 can be located within the single-stranded region 136 of the step-loop structure 132. The adaptor 130 can be combined with a double-stranded DNA fragment 140 having a plus strand 140a and a minus strand 140b to provide the double-stranded molecule 142.

Referring to FIG. 5, in some embodiments, an adaptor 144 comprises two strands 144a and 144b sharing at least one region of substantial complementarity forming at least one double-stranded region 146; and having at least one region of little or no complementarity forming at least one single-stranded region 148. In some embodiments, the adaptor 144 is comprised of two strands forming a structure consisting of two double-stranded regions 146 flanking a single-stranded region 148. As in the case of the adaptor 130 in FIG. 4, each strand of the adaptor 144 in FIG. 5 can include a single primer binding site (not shown) where sequencing is to be initiated. In one example, the primer binding site can be located within the single-stranded region 148. The adaptor 144 can be combined with a double-stranded DNA fragment 150 having a plus strand 150a and a minus strand 150b to provide the double-stranded molecule 152.

In some embodiments, the double-stranded region of the adaptor is used for ligation to a double-stranded or a single-stranded target nucleic acid. In other embodiments, the single-stranded portion of the adaptor is ligated to a double-stranded or a single-stranded target nucleic acid.

Figure 2:
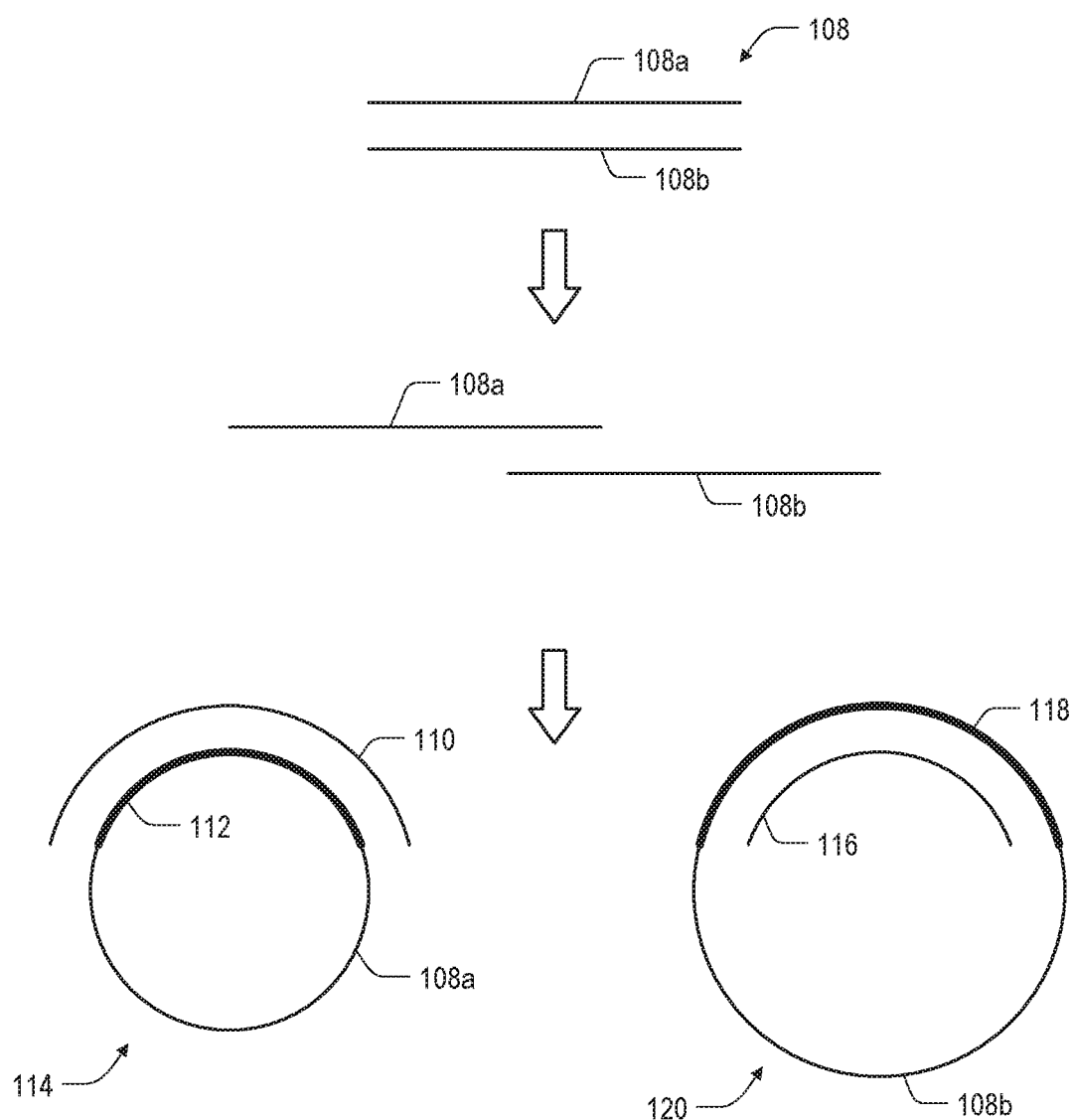
FIG. 2 is a diagram of a prior art method of assembling a circular molecule using splint ligation.

In some embodiments, ligating single-stranded nucleic acids is performed using splint oligonucleotides see e.g., U.S. Application Pub. No. 20120003657. For example, with reference to FIG. 2, a double-stranded DNA fragment 108 having a plus strand 108a and a minus strand 108b can be denatured to provide two single-stranded molecules. Thereafter, a first splint oligo 110 that is complementary to the ends 112 of the plus strand 108a can be annealed to with the plus strand 108a followed by intramolecular ligation of the ends of the plus strand 108a to provide a circularized product 114. Similarly, a second splint oligo 116 that is complementary to the ends 118 of the minus strand 108b can be annealed to with the minus strand 108b followed by intramolecular ligation of the ends of the minus strand 108b to provide a circularized product 120. In other embodiments, ligating single-stranded nucleic acids or partially single-stranded nucleic acids is performed using 5'- and 3'-end single-stranded regions (overhangs) see e.g., U.S. Application Pub. No. 20140193860.

In some embodiments, the adaptor comprises one or more barcodes: a multiplex sample ID (MID), a unique ID (UID) or a combination of a UID and an MID. In some embodiments, a single barcode is used as both UID and MID.

In some embodiments, each strand of the adaptor comprises a primer binding site for a universal primer, e.g., a universal sequencing primer. In some embodiments, one primer binding site is located on each strand in the single-stranded portion of the adaptor molecule (FIGS. 4, 5). In some embodiments, one primer binding site is located on each strand in the double-stranded portion of the adaptor molecule (FIG. 3). The binding sites located on separate strands are not identical, i.e., each strand has a binding site for a different primer. In some embodiments, only one strand of the adaptor carries a primer binding site.

In some embodiments, the adaptor molecules are assembled in vitro by combining two in vitro synthesized artificial oligonucleotides. In some embodiments, the oligonucleotides are in vitro synthesized naturally-occurring sequences known to possess the desired secondary structure. In some embodiments, the oligonucleotides are isolated naturally occurring molecules or isolated non naturally-occurring molecules.

In some embodiments, the invention utilizes enzymes. The enzymes include a DNA polymerase (including sequencing polymerase), a DNA ligase, a polynucleotide kinase, a terminal transferase, optionally Uracil-N-DNA glycosylase, exonuclease, and endonuclease, i.e., AP Lyase.

In some embodiments, the circular joint molecule containing the target nucleic acid is sequenced. The universal primer can be extended with a sequencing polymerase thereby determining the sequence of the double-stranded target nucleic acid. In some embodiments, the sequencing is sequencing by synthesis, including single molecule sequencing or any sequencing of nucleic acids or nucleic acid derivatives. The sequencing technology may include PacBio® RS System, a nanopore sequencing system, or a tunneling recognition sequencing system or any sequencing system where continuous reading of a template is possible and desired. Each strand is sequenced independently. In some embodiments, each strand is sequenced multiple times in a single read, e.g., by rolling circle replication.

In some embodiments, the sequencing data is corrected for errors using barcodes present in adaptors. In some embodiments, Unique Molecular IDs (UIDs) are used to eliminate sequencing errors present in some but not all copies of the same original molecule as identified by the UID. In some embodiments, UIDs are used to obtain a consensus sequence using sequence data from both strands of a single target molecule as identified by matching the two UIDs present in the adaptor.

In some embodiments, the DNA polymerase possesses strand displacement activity and does not have a 5'-3-exonuclease activity. In some embodiments, Phi29 polymerase and its derivatives are used. See U.S. Pat. Nos. 5,001,050, 5,576,204, 7,858,747 and 8,921,086.

In some embodiments, the invention also utilizes a DNA ligase. In some embodiments, T4 DNA ligase or E. coli DNA ligase is used.

In some embodiments, the invention also utilizes a template-independent DNA polymerase, e.g., a terminal transferase. In some embodiments, the invention uses a mammalian terminal transferase.

EXAMPLES

Example 1 (Prophetic). Preparing Circular Joint Molecules Using a Double-Stranded Adaptor In this experiment, the double-stranded target DNA is obtained. The DNA is fragmented to suitable size in vitro or is naturally fragmented. An adaptor is a double-stranded molecule comprising a primer binding site on each strand. (FIG. 3). The adaptor and the target nucleic acid molecules are present at a relative concentration of 200/1 that favors the ligation of a single adaptor to each template. Both ends of the target nucleic acid are filled in and rendered blunt by a nucleic acid polymerase. Optionally, a single nucleotide is added to the 3'-ends of the adaptor molecule and a complementary single nucleotide is added to the target DNA. These steps are performed using KAPA HyperPlus kit. (Kapa Biosystems, Wilmington, Mass.) A single adaptor is ligated to each target DNA to create a joint molecule. A single sequencing primer is complementary to the same primer binding site on both strands of the adaptor or two binding sites are different and each is complementary to one of the two primers. Sequencing proceeds as intended by the manufacturer of the sequencing instrument. The sequencing data is corrected for errors by eliminating sequencing variations present in some but not all copies of the same original molecule as identified by the UID. The sequencing data is further corrected by obtaining a consensus sequence using sequence data from both strands of a single target molecule as identified by matching the two UIDs present in the adaptor.

Example 2 (Prophetic). Preparing Circular Joint Molecules Using a Stem-Loop Adaptor In this experiment, the double-stranded target DNA is obtained. The adaptor is a double-stranded molecule having two double-stranded regions flanking a single-stranded region wherein each strand forms a stem-loop structure. (FIG. 4). The adaptor and the target nucleic acid are processed and ligated as described in Example 1. A single adaptor is ligated to each target DNA to create a joint molecule. A single sequencing primer is complementary to the same primer binding site in the loop portion of both strands of the adaptor or two binding sites are different and each is complementary to one of the two primers. Sequencing proceeds as intended by the manufacturer of the sequencing instrument The sequencing data is corrected for errors by eliminating sequencing variations present in some but not all copies of the same original molecule as identified by the UID. The sequencing data is further corrected by obtaining a consensus sequence using sequence data from both strands of a single target molecule as identified by matching the two UIDs present in the adaptor.

Example 3 (Prophetic) Preparing Circular Joint Molecules Using a Partially Single-Stranded Adaptor In this experiment, the double-stranded target DNA is obtained. The adaptor is a double-stranded molecule having two double-stranded regions flanking a single-stranded region where the strands are not hybridized to each other. (FIG. 5). The adaptor and the target nucleic acid are processed and ligated as described in Example 1. A single adaptor is ligated to each target DNA to create a joint molecule. A single sequencing primer is complementary to the same primer binding site in the unhybridized portion of both strands of the adaptor or two binding sites are different and each is complementary to one of the two primers. Sequencing proceeds as intended by the manufacturer of the sequencing instrument.

The sequencing data is corrected for errors by eliminating sequencing variations present in some but not all copies of the same original molecule as identified by the UID. The sequencing data is further corrected by obtaining a consensus sequence using sequence data from both strands of a single target molecule as identified by matching the two UIDs present in the adaptor.

The invention claimed is:

1. A method of preparing a target nucleic acid for sequencing comprising
    (a) contacting a sample comprising a target nucleic acid with an adaptor molecule comprising two strands which form two duplex regions flanking at least one stem-loop structure, each stem-loop structure comprising a duplex stem region and a non-duplex loop region, the non-duplex region comprising at least one universal primer binding site;
    (b) ligating the adaptor molecule to the target nucleic acid to form a double-stranded circular joint molecule comprising the non-duplex region with the at least one universal primer binding site.

2. A method of sequencing the target nucleic acid prepared by the method of claim 1, comprising
    (c) contacting the joint molecule formed in step (b) with a DNA polymerase and a universal primer complementary to the primer binding site;
    (d) extending the universal primer thereby determining the sequence of the target nucleic acid via sequencing by synthesis.

3. The method of claim 1, wherein each strand of the adaptor comprises one primer binding site.

4. The method of claim 1, comprising prior to step (a), a step of adding in a template-independent manner, a nucleotide to the 3'-termini of the target nucleic acid and a complementary nucleotide to the 3'-termini of the adaptor molecule thereby creating cohesive ends.

5. The method of claim 1, comprising prior to step (a) a step of digesting the target nucleic acid and the adaptor molecule with a restriction endonuclease to generate compatible cohesive ends.

6. The method of claim 1, comprising prior to step (a) a step of digesting a step digesting the 3'-termini of the target nucleic acid and the adaptor molecule with an exonuclease.

7. The method of claim 1, wherein the target nucleic acid and the adaptor molecule contain uracil bases and the method comprises prior to step (a), a step of contacting the target nucleic acid and the adaptor molecule with an N-glycosylase and an AP-lyase.

8. The method of claim 7, wherein the target nucleic acid and the adaptor molecule are contacted with Uracil-DNA-glycosylase and Endonuclease VIII.

9. The method of claim 8, wherein the target nucleic acid and the adaptor molecule are contacted with Uracil-DNA-glycosylase and a polyamine compound at elevated temperature.

10. The method of claim 1, wherein the adaptor comprises one or more barcodes, a Unique Identifier (UID), Multiplex Identifier (MID) or a combination thereof.

* * * * *